US005633162A

United States Patent [19]

Keen et al.

[11] Patent Number: 5,633,162

[45] Date of Patent: May 27, 1997

[54] METHOD FOR CULTURING CHINESE HAMSTER OVARY CELLS

[75] Inventors: Michael J. Keen; Nicholas T. Rapson, both of Beckenham, England

[73] Assignee: Glaxo Wellcome Inc., Research Triangle Park, N.C.

[21] Appl. No.: 205,379

[22] Filed: Mar. 4, 1994

Related U.S. Application Data

[63] Continuation of Ser. No. 991,717, Dec. 18, 1992, Pat. No. 5,316,938, which is a continuation of Ser. No. 777,729, Oct. 16, 1991, abandoned.

[30] Foreign Application Priority Data

Oct. 17, 1990 [GB] United Kingdom ................. 9022545

[51] Int. Cl.⁶ ............................................. C12N 5/00
[52] U.S. Cl. ..................... 435/384; 435/386; 435/387
[58] Field of Search .......................... 435/240.1, 240.3, 435/240.31

[56] References Cited

U.S. PATENT DOCUMENTS

| 4,767,704 | 8/1988 | Cleveland et al. ............... 435/68 |
| 5,063,157 | 11/1991 | Stockinger ....................... 435/240.2 |
| 5,122,469 | 6/1992 | Mather et al. ................... 435/240.2 |

FOREIGN PATENT DOCUMENTS

| 0239400 | 9/1987 | European Pat. Off. . |
| 0307247 | 3/1989 | European Pat. Off. . |
| 0316068 | 5/1989 | European Pat. Off. . |
| 0328404 | 8/1989 | European Pat. Off. . |
| 0389786 | 10/1990 | European Pat. Off. . |
| 0390327 | 10/1990 | European Pat. Off. . |
| 8800967 | 2/1988 | WIPO . |

OTHER PUBLICATIONS

V. Feys, et al., *Chemical Abstracts*, vol. 108, No. 23, Jun. 6, 1988, p. 514, col. 2, abstract 202886c.

M. Tsujimoto et al., *Journal of Biochemistry*, vol. 106, 1989, pp. 23–28.

G. Zettlweissl et al., *Biotechnology*, vol. 5, Jul. 1987, pp. 720–725.

M.J. Page et al., *Biotechnology*, vol. 9, Jan. 1991, pp. 64–68.

Mendiaz, E., et al. (1986) In Vitro. Cell. Dev. Biol. 22: 66–74.

Gasser, F. (1985) id., 21: 588–92.

McCormick, F., et al. (1984), "Inducible expression of amplified human beta . . . " *Molec. Cell Biol.* (4(1): 166–172.

Kaufman, R.J. et al. (1985), "Coamplification and coexpression of human tissue–type plasminogen . . . " *Molec. Cell Biol.* 5(7):1750–59.

Urblan, G and L.A. Chasin (1980). "Isolation of Chinese hamster cell mutants . . . " *Proc. Natl. Acad. Sci. USA* 77(7):4216–20.

Freshney, R.I. (1988). *Culture of Animal Cells.* Alan R. Liss, New York USA, pp. 70–83.

Primary Examiner—John W. Rollins
Assistant Examiner—Deborah K. Ware
Attorney, Agent, or Firm—Nixon & Vanderhye

[57] ABSTRACT

A biochemically defined culture medium for culturing engineered Chinese hamster ovary (CHO) cell lines, which is essentially free from protein, lipid and carbohydrate isolated from an animal source, having water, an osmolality regulator, a buffer, an energy source, amino acids including L-glutamine, an inorganic or recombinant iron source, and a synthetic or recombinant growth factor, and optionally non-ferrous metal ions vitamins and cofactors. Also cells adapted to grow in such a culture medium.

18 Claims, 2 Drawing Sheets

METHOD FOR CULTURING CHINESE HAMSTER OVARY CELLS

This is a continuation of application Ser. No. 07/991,717 filed Dec. 18, 1992, now U.S. Pat. No. 5,316,938 which is a continuation of Ser. No. 07/777,729, filed Oct. 16, 1991, now abandoned.

The present invention relates to a biochemically defined culture medium for culturing Chinese hamster ovary (CHO) cell lines and cells adapted to grow in the culture medium.

Chinese hamster ovary cells (CHO) were first cultured by Puck (J. Exp. Med. 108, 945, 1958) from a biopsy of an ovary from a female Chinese hamster. From these original cells various workers have cloned a number of sub-lines with various deficiencies, one of which, CHO-K1, is proline-requiring and is diploid for the dihydrofolate reductase (dhfr) gene. From this cell line a dhfr$^-$ CHO cell line (CHO DUK B11) was developed (PNAS 77, 1980, 4216–4220) which is characterised by the loss of dhfr function as a consequence of a mutation in one dhfr gene and the subsequent loss of the other gene. These cells are functionally dhfr$^-$. Other OHO DUK sub-lines have been derived which are also phenotypically dhfr$^-$. CHO cells which are dhfr$^-$ cannot grow without nucleotide precursors such as thymidine, hypoxanthine, or the equivalent nucleosides.

Various proteins have been expressed in such CHO cells including *E. coli* XGPRT gene (J. Mol. App. Gen. 1981, 1, 165–175), human tissue-type plasminogen activator (Mol. & Cell Biol. 5, 170–1759, 1985), human immune (γ) interferon (PNAS 80 pp 4654–4658), and human beta interferon (Molecular and Cellular Biology 4, 166–172, 1984). A dhfr$^-$ CHO cell line is transfected with a product gene and a dhfr gene which enables selection of CHO cell transformants of the dhfr$^+$ phenotype. Selection is carried out by culturing the colonies in media devoid of thymidine and hypoxanthine, the absence of which prevents untransformed cells from growing. The transformants usually express low levels of the product gene by virtue of co-integration of both transfected genes. The expression levels for the product gene may be increased by amplification using methotrexate. This drug is a direct inhibitor of the dhfr enzyme and allows isolation of resistant colonies which have amplified their dhfr gene copy number sufficiently to survive under these conditions. Since the dhfr and product genes are usually closely linked in the original transformants, there is normally concomitant amplification resulting in increased expression of the desired product gene.

A different system of selection and amplification is provided by the glutamine synthetase selectable marker (or GS system) which is described in WO87/04462. CHO cells which have been successfully transfected with the gene encoding the GS enzyme and the desired antibody gene can be selected by culturing colonies in media devoid of glutamine and amplifying by the addition of methionine sulphoximine (Msx) as described in PCT published application number WO87/04462.

Engineered CHO cells (those in which a CHO cell line is transfected with a product gene and a selectable marker gene) are routinely grown in culture media containing serum. (References: J. Mol. App. Gen. 1981, 1, 165–175; Mol. & Cell Biol. 5, 1750–1759, 1985; PNAS 80 pp 4654–4658; Molecular and Cellular Biology 4, 166–172, 1984). Fetal bovine serum (FBS) is probably the most extensively utilised serum for mammalian cell culture, although other mammalian sera are used. However, the use of serum poses a number of problems. Serum is an expensive commodity which is not readily available in amounts required for commercial production. It is also a biochemically undefined material. Serum is known to contain many major components including albumin and transferrin and also minor components many of which have not been fully identified nor their action determined, thus serum will differ from batch to batch possibly requiring testing to determine levels of the various components and their effect on the cells. Frequently, serum is contaminated with microorganisms such as viruses and mycoplasma many of which may be harmless but will represent an additional unknown factor. This problem has become more acute in recent years with the emergence of Bovine Spongiform Encephalopathy (BSE). Despite improvements in screening, regulatory authorities are likely to require the sourcing of bovine products from those areas which are free from (BSE) infections. Furthermore, the presence of animal proteins in culture media can require lengthy purification procedures, in particular the presence of bovine antibodies in bovine serum albumin (BSA) makes purification of the desired antibodies expressed by the recombinant CHO cell line, extremely difficult. Removal of bovine antibody from the medium prior to use is possible but this and the additional product testing required, adds greatly to the everall cost of production of the product. Consequently, there has been much research into finding a culture medium devoid of animal components which will support cellular growth, especially of CHO cells. Unfortunately, the problems associated with the provision of such a medium are themselves numerous. CHO cells do not readily grow in serum-free conditions. In addition, the removal of serum may also remove those components that provide cell protection and detoxifying activity.

A culture medium which is serum-free but not free from animal components is described by Mendiaz et al (In Vitro Cellular & Development Biology Vol.22, No.2, 1986) for use in the culture of CHO K1 cells. The medium is a modification of the medium developed by Ham (Microbiology 53 1965 288–293) which is known as "Ham's F12". Other examples of media have been based on Ham's F12 medium for example as disclosed in EPA390327 and EP325190. These media contain transferrin as the serum substitute, but transferrin is derived from an animal source, so the resulting media do not overcome the contamination problems associated with the use of serum.

A further problem which arises with the use of serum-free media is that of supporting recombinant CHO cells to enable growth and expression of product. Media based on Ham's F12 which are not supplemented with serum are generally not rich enough to support full growth or expression.

Engineered CHO cells are also difficult to grow in suspension. It is highly desirable to achieve growth in suspension when using the cells to express a product such as an antibody. For production of a biological protein on a commercial scale it is preferable to be able to support growth in fermenters which range from 1 liter glass vessels to multi-thousand liter stainless steel tanks. A suitable medium must be able to support the cells against sheer forces from blade impellers or turbines and from effects of sparging (ie: supplying air, oxygen and $CO_2$ in bubble form directly to the medium).

The present invention therefore provides a biochemically defined culture medium for culturing engineered CHO cells which is essentially free from protein, lipid and carbohydrate isolated from an animal source, comprising water, an osmolality regulator, a buffer, an energy source, amino acids including L-glutamine, an inorganic or recombinant iron source and a recombinant or synthetic growth factor and optionally non-ferrous metal ions, vitamins and cofactors.

The components of the medium are mostly inorganic, synthetic or recombinant and as such are not obtained directly from any animal source. Some components may be obtained from a plant or bacterial source. Recombinant components are prepared under highly pure conditions to minimise the risk of contamination from the parent tissue passing to the cells used to produce the components. Further purification steps may be employed to remove cell proteins. Thus, a medium which is essentially free from all protein, lipid and carbohydrate isolated from an animal source, can be achieved. The preferred culture medium of the invention contains no protein, lipid and carbohydrate isolated from an animal source.

It is advantageous to maintain osmolality in the range 200–30 milli-Osmols (mOsm) preferably in the range 290–350 mOsm. Osmolality regulators are generally salts. Those which may be used in the medium include NaCl, KCl, $KNO_3$.

Buffers of use in the medium to maintain the pH in the range 6.5–7.5 most preferably around pH 7.0. Buffers of use in the medium include carbonates such as $NaHCO_3$; also chlorides, sulphates and phosphates such as $CaCl_2 2H_2O$, $MgSO_4 7H_2O$, $NaH_2PO_4 2H_2O$, or sodium pyruvate, such buffers are generally present in an amount 50–500 mg/liter. Other buffers, such as N-[2-hydroxyethyl]piperazine-N'-[2-ethanesul-phonic acid] otherwise known as HEPES and 3-[N-Morpholino]-propanesul-fonic acid otherwise known as MOPS are generally present in an amount 1000–10,000 mg/liter.

The energy source of use in the medium is generally present in an amount 1000–10,000 mg/liter and is preferably a monosaccharide such as manose, fructose, galactose or maltose most preferably glucose, particularly D-glucose.

The non-ferous metal ions optionally of use in the medium include magnesium, copper and zinc; also sodium, potassium and selenium. The ions are generally added to the medium in the form of salts such as chlorides and sulphates. The amounts are typically similar to those provided in the ISCOVES medium set out in Table 1 but clearly may be varied.

Vitamins and enzyme co-factor vitamins (co-factors) optionally of use in the medium include Vitamin B6 (pyridoxine), Vitamin B12 (cyanocobalamin) and Vitamin K (biotin) present in an amount 0.01–0.5 mg/liter; Vitamin C (ascorbic acid) present in an amount 10–30 mg/liter, Vitamin B2 (riboflavin) present in an amount 0.1–1.0 mg/liter and Vitamin B1 (thiamine), nicotin amide, Vitamin B5 (D calcium pentothenate), folic acid, i-inositol generally present in an amount 0.2–8.0 mg/liter.

It is preferable to include in the basal medium a lipid factor such as choline chloride, lipoic acid, oleic acid, phosphatidylcholine or methyl lineoleate, generally in an amount 0.05–10 mg/liter. Compounds involved in lipid production for example alcoholamines such as ethanolamine may also be added.

It is preferable to include additional amino acids in the medium selected from:

| Amino Acid | Preferred mg/liter |
|---|---|
| L-Alanine | 20–50 |
| L-Arginine (HCl) | 50–100 |
| L-Asparagine ($H_2O$) | 20–50 |
| L-Aspartic Acid | 20–50 |

-continued

| Amino Acid | Preferred mg/liter |
|---|---|
| L-Cystine (disodium salt) | 50–100 |
| L-Glutamic acid | 50–100 |
| L-Glutamine | 400–600 |
| Glycine | 20–50 |
| L-Histidine ($HCl.H_2O$) | 30–60 |
| L-Isoleucine | 50–150 |
| L-Leucine | 50–150 |
| L-Lysine (HCl) | 100–200 |
| L-Methionine | 20–50 |
| L-Phenylalanine | 40–80 |
| L-Proline | 30–60 |
| L-Serine | 30–60 |
| L-Threonine | 50–120 |
| L-Tryptophan | 10–20 |
| L-Tyrosine (disodium salt) | 50–120 |
| L-Valine | 80–120 |

The bracketed forms are preferred.

The amino acids are preferably of synthetic origin. The amounts which are usually included vary for each amino acid but are generally in the range 10–150 mg/ml. However, L-glutamine is generally present at much higher concentration preferably in the range 400–600 mg/ml.

It may be advantageous to include in the medium a pH indicator for example Phenol red sodium salt for example at 5–50 mg/liter.

Medium A as set out in Table 1, is an example of a medium which provides the preferred quantities of water, osmolality regulator, buffer, energy source, amino acids, non-ferrous metal ions, vitamins and co-factors as a basis for a culture medium according to the invention. This medium does not contain any hypoxanthine or thymidine and is commercially available from GIBCO Ltd., Unit 4, Cowley Mill Td. Est., Uxbridge UB8 2YG. It is similar to a published culture medium (Iscoves and Melcher (1978) J. Exp. Med. 1. 47,923) but does not contain any bovine serum albumin, pure human transferrin or soyabean lecithin.

TABLE 1

Medium A (modification of Iscoves' DMEM lacking albumin, transferrin and lecithin)

| Ingredient | mg/liter |
|---|---|
| L-Alanine | 25.00 |
| L-Arginine HCl | 84.00 |
| L-Asparagine $H_2O$ | 28.40 |
| L-Aspartic Acid | 30.00 |
| L-Cystine | 70.00 |
| L-Glutamic acid | 75.00 |
| L-Glutamine | 584.00 |
| Glycine | 30.00 |
| L-Histidine $HCl.H_2O$ | 42.00 |
| L-Isoleucine | 105.00 |
| L-Leucine | 105.00 |
| L-Lysine HCl | 146.00 |
| L-Methionine | 30.00 |
| L-Phenylalanine | 66.00 |
| L-Proline | 40.00 |
| L-Serine | 42.00 |
| L-Threonine | 95.00 |
| L-Tryptophan | 16.00 |
| L-Tyrosine disodium salt | 104.20 |
| L-Valine | 94.00 |
| Biotin | 0.013 |
| D.Calcium Pantothenate | 4.00 |
| Choline chloride | 4.00 |
| Folic acid | 4.00 |
| i-Inositol | 7.20 |
| Nicotinamide | 4.00 |

TABLE 1-continued

Medium A (modification of Iscoves' DMEM lacking albumin, transferrin and lecithin)

| Ingredient | mg/liter |
| --- | --- |
| Pyridoxal HCl | 4.00 |
| Riboflavin | 0.40 |
| Thiamin HCl | 4.00 |
| Vitamin B 12 | 0.013 |
| $CaCl_2 2H_2O$ | 219.00 |
| KCl | 330.00 |
| $KNO_3$ | 0.076 |
| $MgSO_4 7H_2O$ | 200.00 |
| NaCl | 4505.00 |
| $NaHCO_3$ | 3024.00 |
| $NaH_2PO_4 2H_2O$ | 141.30 |
| D-Glucose | 4500.00 |
| HEPES | 5958.00 |
| Phenol red sodium salt | 15.00 |
| Sodium pyruvate | 110.00 |
| Sodium selenite | 0.017 |

DMEM modification of Iscoves N and Melcher (1978), J. Exp. Med. 1, 47, 923.

It is preferable to add to the medium, selenium (optionally in the form of sodium selenite) generally in an amount 0.01–0.2 mg/liter or L-Ascorbic acid generally in an amount 20–50 mg/liter to help minimise the potential toxic effects of ferrous or ferric ions, and oxygen. Further use of chelating agents such as citrate or Ethylenediaminetetraacetic acid (EDTA) or a free radical scavenger such as α-Tocepherol (vitamin E) are advantageous in reducing free radical damage.

Antibiotics such as polymyxin, neomycin, penicillin or streptomycin may be added to the medium to prevent bacterial contamination. These are usually included in an amount 10,000–100,000 Iu/liter.

Growth factors which may be added to the basal medium are synthetic or recombinant and include insulin. Other factors such as platelet-derived growth factor (PDGF), thyroxtne $T_3$, thrombin, interleukins such as IL2 and IL6, progesterone, hydrocortisone and vitamin E may be included. Folic acid, vitamin B6 and vitamin B12 which are involved in the folate pathway may be added to enhance the growth of cells.

The peptide hormone insulin (which in the present context includes analogues thereof such as Nucellin® (recombinant insulin, Eli Lilly) is advantageously obtained by recombinant DNA techniques but is not isolated from an animal source. It is preferably added to the medium in an amount 5 µg–5 mg/liter. Nucellin is the preferred form of insulin for use in the invention.

The non-animal derived iron source to supplement the medium, is preferably inorganic and present in an amount 0.25–5 mg/liter. Examples include ferric and ferrous salts such as ferric citrate or ferrous sulphate. The chelated salts such as ferric citrate and ferric ammonium citrate are preferred. However, any iron source may be used which is not isolated from an animal source, for example, chemical iron chelators or recombinant protein iron carriers.

The concentration of ferric or ferrous ions should be carefully controlled as these may help generate superoxides and free radicals in the medium, which may damage not only the cells themselves, but medium components and the desired end product.

It is also preferable to add to the medium, a compound such as putrescine, advantageously as a salt such as HCl, which is known to play a role in maintaining the structure of the endoplasmic reticulum and to be required by certain CHO cell lines to support growth. Putrescine or a salt thereof is preferably added in an amount 0.01–1.0 mg/liter.

Serum-free media disclosed to date contain hypoxanthine or thymidine. This could bypass the selection pressure placed on the dhfr selection and amplification system as previously disclosed. The result may be loss of genetic material specifying the product and the dhfr genes. Therefore, In another aspect of the invention there is provided a culture medium for the growth of engineered dhfr⁻ CHO cells in accordance with the invention, essentially free from hypoxanthine and/or thymidine.

The culture medium of the present invention supports CHO cell growth and when supplemented with an appropriate agent such as methotrexate for the dhfr system usually in an amount 0.1–5.0 µM, (or MSX for the GS system), allow full selection pressure to be exerted on the cells. It will be understood that hypoxanthine and thymidine at concentrations which are insufficient to bypass selection of the dhfr system may be present in the medium, but the presence of these two nucleotide precursors is not preferred for use with the present invention.

In large scale fermentera, mammalian cells are particularly susceptible to sheer forces arising from the sparging of the vessel with gases and the mixing with the impeller. To minimise the occurrence of cellular damage it is advantageous for the medium to contain a cell protectant such as polyethylene glycol, polyvinyl alcohols or pluronic polyols. Of these, Pluronic® (polyol, BASF Wyandotte Corp.) polyol F68 is preferred since unlike polyvinyl alcohols this is a non-toxic substance and unlike polyethylene glycols does not interfere with downstream purification.

Further improvements in CHO cell growth may be obtained by supplementing the medium with a peptide digest, hydrolysates or extracts, such as Tryprone, casein hydrolysate, yeast extract, or preferably papain digested soya peptone. The preferred amounts are 1%–0.025% w/v, most preferably 0.25% w/v.

The media of the invention for culturing recombinant CHO cells are capable of supporting the growth and secretion of product from such cells in suspension in small and large scale fermenters, static cultures and/or spinners. The culture medium according to the invention is also capable of supporting growth of cells at high cell density namely greater than $1 \times 10^5$ cells/ml up to or greater than $1.5 \times 10^6$ cells/ml and product secretion of 30 mg/l up to greater than 150 mg/l. The medium according to the invention is also capable of supporting this growth and product secretion over multiple passages lasting upto or greater than 6 months.

The medium is preferred for the production of all types of antibodies natural and altered. The invention therefore includes production of human antibodies wherein the amino acid sequences of the heavy and light chains are homologous with those sequences of antibodies produced by human lymphocytes in vivo or in vitro by hybridomas. Also provided are hybrid antibodies in which the heavy and light chains are homologous to a natural antibody but are combined in a way that would not occur naturally. For example, a bispecific antibody has antigen binding sites specific to more than one antigen. The constant region of the antibody may relate to one or other of the antigen binding regions or may be from a further antibody. Altered antibodies, for example chimaeric antibodies have variable regions from one antibody and constant regions from another. Thus, chimaeric antibodies may be species/species chimaeras or class/class chimaeras. Such chimaeric antibodies may have one or more further modifications to improve antigen binding ability or to alter effector functioning. Humanised or CDR-grafted antibodies (EP 239400) are embraced within the invention, in particular Campath 1H (EP328404) (Campath is a TM of The Wellcome Foundation) also composite antibodies, wherein parts of the hypervariable regions in addition to the CDRs are tranferred to the human framework. Additional amino acids in the framework or constant regions of such antibodies may be altered. The invention further includes the production of Feb fragments which are roughly equivalent to the Y branch portions of the heavy and light chains; this includes incomplete fragments or fragments including part of the Fc region.

In a further aspect of the invention there is provided an engineered CHO cell adapted to grow in a medium according to the invention. In particular a CHO cell engineered to express proteins such as tissue plasminogen activator or antibodies as defined above. In particular the invention provides a dhfr- CHO cell line transfected with a gene encoding a biologically active protein and a dhfr selectable marker gene, adapted to grow in a culture medium according to the invention. The protein is preferably an antibody as defined above.

The ingredients of the culture medium may be added in any order but it is preferable to add the iron source and when used, tyrosine, last to avoid precipitation.

Accompanying Figures are for illustration only.

EXAMPLE 1

Figure 1:
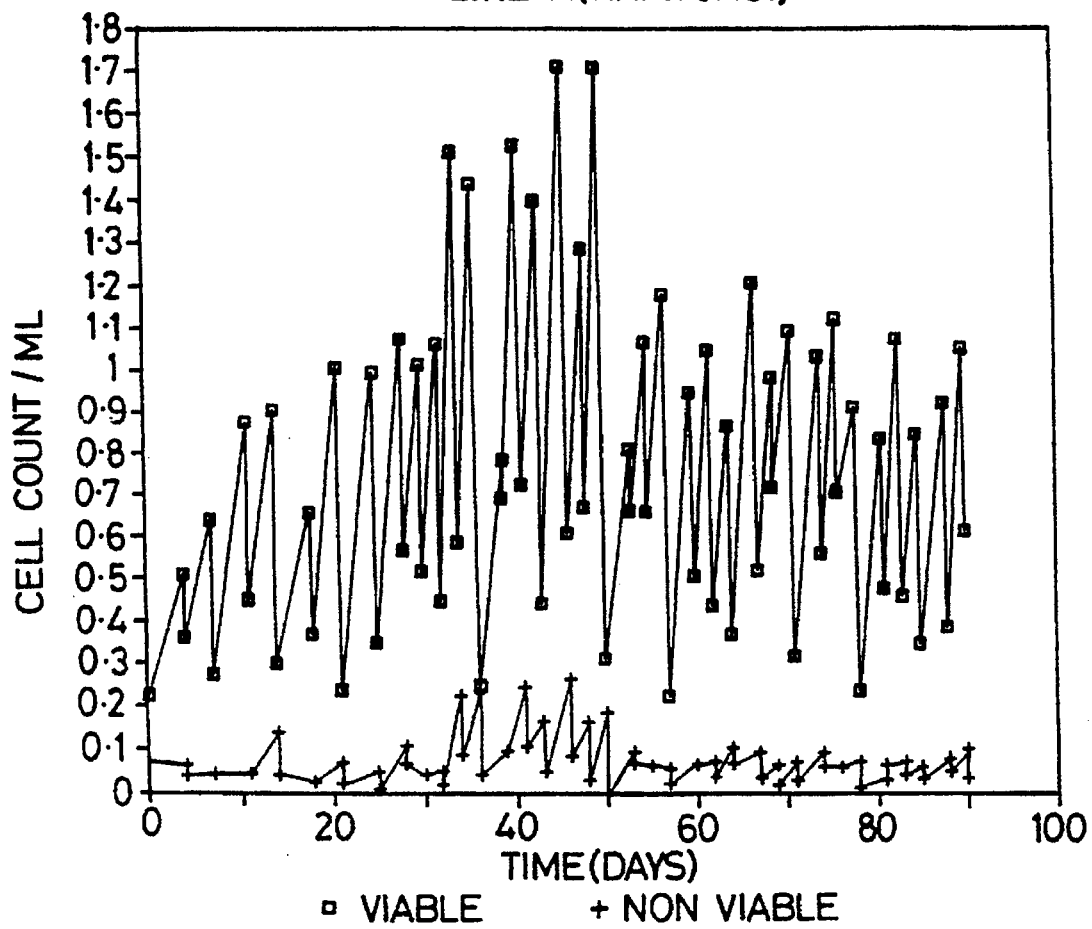
FIG. 1 shows growth of C1H 3D11* 44 in WCM5 (protein-free medium) in a 1 liter fermenter measured as cell count/ml over 90 days.

Formulation for medium WCM4,

Medium A: (Iscoves modification of DMEM without BSA, transferrin and lecithin as set out in Table 1).

| 5 ml/liter | 200 mM L glutamine |
|---|---|
| +50 mg/liter | L proline |
| +50 mg/liter | L threonine |
| +50 mg/liter | L methionine |
| +50 mg/liter | L cysteine |
| +50 mg/liter | L tyrosine |
| +25 mg · liter | ascorbic acid |
| +0.062 mg · liter | vitamin B6 |
| +1.36 mg · liter | vitamin B12 |
| +0.2 mg/liter | lipoic acid |
| +0.088 mg/liter | methyl linoleate |
| +1 µM | methotrexate |
| +1 mg/liter | FeSO$_4$ |
| +1 mg/liter | ZnSO$_4$ |
| +0.0025 mg/liter | CuSO$_4$ |
| +5 mg/liter | recombinant insulin (Nucellin) |
| +50,000 Iu/liter | polymyxin |
| +20,000 Iu/liter | neomycin |
| +0.16 mg/liter | putrescine-2 HCL. |

This medium does not contain hypoxanthine, thymidine or folinic acid which can bypass methotrexate selection. The medium does contain glycine which cannot by itself bypass selection. Therefore, this medium maintains full selection for methotrexate resistance.

EXAMPLE 2

Formulation for Medium WGM5

Medmium A: (Iscoves modification of DMEM without BSA, transferrin or lecithin).

| + | 5 ml/liter | 200 mM L glutamine |
|---|---|---|
| + | 50 mg/liter | L proline |
| + | 50 mg/liter | L threonine |
| + | 50 mg/liter | L methionine |
| + | 50 mg/liter | L cysteine |
| + | 50 mg/liter | L tyrosine |
| + | 25 mg/liter | L ascorbic acid |
| + | 0.062 mg · liter | Vitamin B6 |
| + | 1.36 mg · liter | Vitamin B12 |
| + | 2 mg/liter | Ferric citrate |
| + | 1 mg/liter | Zinc sulphate |
| + | 0.0025 mg · lit | Copper sulphate |
| + | 50,000 IU/liter | Polymyxin |
| + | 20,000 IU/liter | Neomycin |
| + | 3 µl/liter | Ethanolamine |
| + | 0.16 mg/liter | Putrescine |
| + | 5 mg/liter | Recombinant Insulin (Nucellin ®) |

EXAMPLE 3

Growth of and Production from C1H 3D11* 44 in WCM4

C1H 3D11* cells are genetically engineered CHO DUK B11 cells (Urlaub and Chasin (1980) PNAS 77, 7 pp 4216–4220). CHO DUK B11 cells cannot produce dihydrofolate reductase (dhfr). These cells were engineered to produce a humanised IgG antibody, Campath 1H (Winter et al., Nature, 1988, 322, 323–327), using plasmid constructs to express heavy and light antibody chains and the mouse dhfr. Expression is amplified and maintained using the folate antagonist methotrate. C1H 3D11* cells growing as a monolayer in Isover+10% FBS Flow, non-essential amino acids, $10^{-6}$M Methotrexate and antibiotics were approximately 90% confluent. These cells were removed from the plastic with trypsin/versene, washed in Iscoves medium without supplements, centrifuged and resuspended at $5 \times 10^4$/ml in WCM4 medium+0.25% peptone+0.1% polyethylene glycol (PEG) 10,000+0.5% fetal bovine serum (FBS) without methotrexate (MTX). Three 25 cm$^2$ flasks were set up with 10 ml of cell suspension+hypoxanthine (H), thymidine (T) or HT. These flasks were incubated at 36.5° C. in 5% CO$_2$ incubator.

After six days, the flasks were pooled and added to an equal volume of WCM4+MTX without peptone or PEG, and were transferred to a 75 cm$^2$ flask.

These cells were used to seed a 500 ml Techner spinner, incubated at 36.5° C. spinning at 40 rpm. Cells continued growing serum free for a period of over five months and although it was-found that the cells needed a period of adaptation, the growth rate and viability steadily improved. The population doubling time was calculated to be 73.1 hours over approximately 7 weeks; this decreased to 47.4 hours over the subsequent 20 days then stabilised. Antibody secretion remained high at levels in excess of 60 µg/ml. It was determined that the gene copy number in these cells did not decrease according to band intensity using Northern blot analysis.

In fermenters, these cells produced antibody in excess of 70 µg/ml and regularly achieved levels of 100 µg/ml or more. The cells are denoted C1H 3D11* 44.

EXAMPLE 4

Growth and Production of CIH 3D11* 44 in WCM5 in a 1 liter fermenter.

C1H 3D11*44 cells from Example 3 which had been growing serum-free for over 2 months were transferred to a SGi 1 liter fermenter with a stainless steel angled paddle turning at 70 rpm. The temperature was set at 37° C., $dO_2$ at 10% and pH control to 7–7.2. The fermenter was seeded on day 0 with $0.22 \times 10^6$ cells/ml in WCM4 (Example 1) with 0.1% polyethylene glycol (PEG) 10,000 and 0.25% soy peptone, and was top gassed with $O_2$. The cells were routinely passaged using fresh medium and a split rate typically between 1 to 2 and 1 to 4.

On day 33 the top gassing was replaced with deep sparging which is can be expected to cause more physical damage to the cells.

On day 50 onwards WCM5 (Example 2) was used together with peptone and PEG instead of WCM4.

Figure 2:
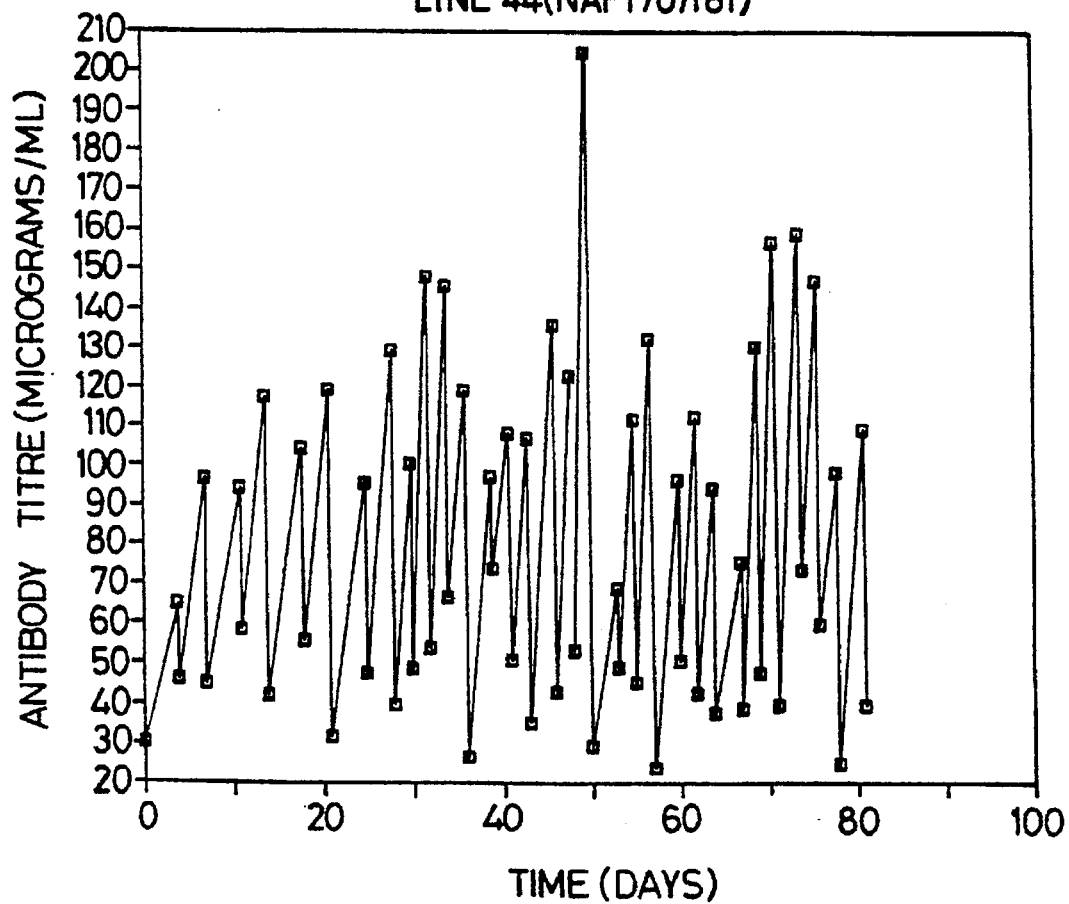
FIG. 2 shows antibody production from C1H 3D11* 44 cells in WCM5 in a 1 liter formenter measured as micrograms of antibody/ml over 80 days.

On day 53 the PEG was replaced with 0.1% Pluronic F68. The resulting growth and antibody levels achieved are shown the the attached graphs (FIGS. 1 and 2), and demonstrate the capacity of the invention to allow protein-free production of antibody in excess of 100 μg/ml in fermenters.

EXAMPLE 5

Growth of CHO AJ19 MCB1 in WCM4 and compared to CHO AJ19 MCB1 grown in serum containing medium Chinese hamster ovary cells, CHO AJ19 MCB1, derived from CHO DUK cells, (Urlaub & Chasin PNAS, 77, 7, pp4216–4220, 1980), were genetically engineered to produce tPA under methotrexate selection. This cell line had been routinely grown in a fermenter as a suspension culture using normal growth medium consisting of RPMI 1640 medium (GIBCO), 2.5% acid hydrolysed adult bovine serum (Imperial), 0.5% Tryptone, 50 IU/ml polymycin, 20 IU/ml neomycin, 500 nM methotrexate (MTX).

Medium WCM4 was formulated to which was added:

46B 0.25% w/v N-Z Soy Peptone (Sigma P1265), 0.1% w/v Polyethylene glycol (PEG) 20,000 (Serva, Carbowax® 20M), 1 uM MTX.

46C 0.25% w/v Yeast extract (Sigma Y0500), 0.1% w/v PEG 20,000 1 uM MTX. In this medium the Iscoves' in CM4 was replaced by RPMI 1640 medium (ICN FLOW).

46D 0.25% w/v Yeast extract, 0.1% w/v PEG 20,000, 1 uM MTX.

46E 0.25% w/v Yeast extract, 0.1% w/v PEG 20,000, 0.25% Fetal bovine serum (Imperial), 1 uM MTX.

The yeast extract, Peptone and PEG were made up as 10% w/v solutions with water (Wellcome media production unit) and filtered through a 0.2 um disposable filter (Gelman, Supor Vac), then diluted for use. The cells were incubated at 37° C. in a humidified incubator containing 5% $CO_2$.

Cells growing in normal growth medium were pelleted by centrifugation at 1200 g +4° C. for 5 minutes, were washed in RPMI 1640 without supplements and pelleted again. The cells were then resuspended at $10^5$ cell/ml in normal growth medium (46A) and the other media (46B, 46C, 46D or 46E). 24 well plates (Costar 16 mm wells) were seeded with 1 ml/well and incubated, at 37° C. in an incubator containing 5% $CO_2$. On days 3, 4, 5 and 6 one well of each was counted using a haemcytometer and trypan blue exclusion. Two further wells of each were harvested, pooled and pelleted at 1200 g +4° C. 5 minutes. The supernatant was separated and stored at −20° C. These samples were subsequently assayed for tPA. On day 6 samples from 46A and 46D only were harvested.

RESULTS tPA specific activities in various crude harvests

Crude material produced in the five different media were tested using a QA validated ELISA assay to measure the tPA antigen concentrations μg/ml using binding to a polyclonal antibody against tPA, and clot lysis assay to measure tPA activity in IU/ml. From these results (Table 2), the specific activities were calculated.

TABLE 2

| EXPERIMENT | DAYS IN CULTURE | CELLCOUNT ×10⁻⁵ VIABLE | CELLCOUNT ×10⁻⁵ NONVIABLE | MEAN tPA ACTIVITY IU/ml (n = 3) | MEAN tPA CONTENT ug/ml (n = 3) | SPECIFIC ACTIVITY MegIU/mg |
|---|---|---|---|---|---|---|
| 46A | 3 | 3.5 | 0.1 | 3051 | 10.51 | 0.290 |
| 46A | 4 | 3.7 | 0.3 | 4841 | 14.85 | 0.326 |
| 46A | 5 | 4.1 | 0.2 | 5306 | 15.52 | 0.335 |
| 46A | 6 | 5.8 | 0.5 | 8235 | 23.22 | 0.355 |
| 46B | 3 | 5.2 | 0.1 | 2552 | 10.44 | 0.244 |
| 46B | 4 | 7.2 | 0.3 | 5310 | 18.58 | 0.286 |
| 46B | 5 | 7.8 | 0.2 | 6230 | 22.19 | 0.281 |
| 46C | 3 | 3.8 | 0.2 | 2779 | 9.61 | 0.289 |
| 46C | 4 | 4.9 | 0.3 | 3536 | 16.54 | 0.214 |
| 46C | 5 | 5.6 | 0.3 | 4639 | 19.88 | 0.233 |
| 46D | 3 | 7.5 | 0.2 | 4650 | 17.66 | 0.263 |
| 46D | 4 | 8.3 | 0.8 | 7369 | 25.99 | 0.285 |
| 46D | 5 | 7.4 | 1.0 | 7882 | 24.26 | 0.325 |
| 46D | 6 | 6.1 | 2.0 | 8095 | 27.06 | 0.299 |
| 46E | 3 | 6.4 | 0.1 | 6262 | 23.85 | 0.263 |
| 46E | 4 | 7.3 | 0.5 | 10180 | 29.70 | 0.343 |
| 46E | 5 | 6.1 | 1.3 | 9080 | 34.25 | 0.265 |

From the above table there was no change of the specific activity in the five different crudes. The yield of tPA from protein free medium B, C and D was nearly equal to the yield of tPA from standard growth medium in group A and E.

Example 6 Continuous growth of CHO AJ19 MCBI in WCM4

CHO AJ19 MCBI in WCM4 cells growing in normal growth medium were pelleted and washed as in Example 5 and were resuspended at $7 \times 10^4$/ml in 500 ml of medium 46B. These cells were transferred to a Techne spinner flask and incubated, as above, stirring at 40 rpm. At various time intervals the cells were counted and subcultured using the same medium. A sample was taken for tPA assay and treated as in Example 5.

The specific activity of tPA in various cell subcultures

The specific activity of supernatants from different pass levels of cells grown in WCM4 with peptone and 0.1% PEG 20K were measured by a combination of ELISA and clot lysis assay. The specific activities of different cell passages are summarised in Table 3.

TABLE 3

| | | CELLCOUNT ×10⁻⁵ | | SPLIT | tPA present in supernatant | | |
|---|---|---|---|---|---|---|---|
| | | | | | conc. ug/ml | tPA ACTIVITY IU/ml | SPECIFIC ACTIVITY |
| DAYS | PASS | VIABLE | NONVIABLE | RATE | (n = 3) | (n = 3) | Meg.U/mg |
| 7 | 1 | 9.75 | 0.65 | 1–10 | ND | ND | ND |
| 10 | 2 | 4.95 | 0.01 | 1–5 | ND | ND | ND |
| 13 | 3 | 6.35 | 0.0 | 1–10 | 22.2 | 8865 | 0.399 |
| 16 | 4 | 3.8 | 0.0 | 1–10 | 7.25 | 1914 | 0.264 |
| 21 | 5 | 7.2 | 0.8 | 1–10 | 15.08 | 4331 | 0.287 |
| 24 | 6 | 4.1 | 0.3 | 1–10 | 8.28 | 2040 | 0.246 |
| 30 | 7 | 5.3 | 0.4 | 1–6 | 7.30 | 2052 | 0.281 |
| 34 | 8 | 5.2 | 0.32 | — | 13.65 | 3518 | 0.258 |
| 36 | 8 | 7.95 | 0.10 | 1–8 | 18.60 | 5327 | 0.286 |
| 37 | 8 | ND | ND | — | 20.68 | 5526 | 0.267 |
| 38 | 8 | | 100% | — | 19.10 | 5474 | 0.287 |
| 38 | 9 | 12.00 | 0.5 | 1–5 | 20.85 | 8348 | 0.400 |
| 43 | 10 | 5.5 | 0.12 | 1–5 | 7.38 | 1888 | 0.256 |
| 48 | 11 | 4.4 | 0.19 | 1–6 | 13.4 | 3143 | 0.235 |
| | 12 | Experiment terminated | | | | | |

ND = not done.

Over a 48 day period, base on the above split rate, one cell could have divided to give $3.77 \times 10^8$ cells. This is equivalent to 31.8 population doublings with a doubling time of 36 hours.

The results of the experiments conducted in Examples 5 and 6 demonstrate that the serum free media of the present invention is capable of supporting cell growth and tPA yield comparable to that achieved in serum containing media.

We claim:

1. A method for growing CHO cells which comprises culturing CHO cells under cell growing conditions in the absence of serum in a medium comprising water, an osmolality regulator, a buffer, an energy source, L-glutamine and at least one additional amino acid, an inorganic, organic or recombinant iron source and a recombinant or synthetic growth factor wherein each component of said medium is obtained from a source other than directly from an animal source.

2. A method for culturing CHO cells in accordance with claim 1 wherein the medium further comprises non-ferrous metals, vitamins or cofactors.

3. A method for culturing CHO cells in accordance with claim 1, wherein the osmolality regulator maintains the medium at 200–350 mOsm.

4. A method for culturing CHO cells in accordance with claim 1, wherein the medium is maintained at a pH in the range of about 6.5 to about 7.5 by the buffer.

5. A method for culturing CHO cells in accordance with claim 1, wherein the concentration of the energy source is within the range of 1000–10,000 mg/liter.

6. A method for culturing CHO cells in accordance with claim 5, wherein the energy source is a monosaccharide.

7. A method for culturing CHO cells in accordance with claim 1, wherein the additional amino acids are selected from the group consisting of L-alanine, L-arginine, L-asparagine, L-aspartic acid, L-cystine, L-glutamic acid, glycine, L-histidine, L-isoleucine, L-leucine, L-lysine, L-methionine, L-phenylalanine, L-proline, L-serine, L-threonine, L-tryptophan, L-tyrosine and L-valine.

8. A method for culturing CHO cells in accordance with claim 1, wherein the concentration of L-glutamine is within the range of 400–600 mg/liter.

9. A method for culturing CHO cells in accordance with claim 2, wherein the medium comprises a lipid factor in an amount of 0.05–10 mg/liter.

10. A method for culturing CHO cells in accordance with claim 1, wherein the iron source is an inorganic ferric or ferrous salt which is provided in a concentration of from 0.25–5 mg/liter.

11. A method for culturing CHO cells in accordance with claim 1, wherein the growth factor comprises recombinant or synthetic insulin, platelet derived growth factor, thyroxine $T_3$, thrombin, interleukin, progesterone, hydrocortisone or vitamin E.

12. A method for culturing CHO cells in accordance with claim 11, wherein the growth factor is recombinant or synthetic insulin.

13. A method for culturing cells in accordance with claim 1, wherein the medium further comprises a peptide digest, hydrolysate or extract.

14. A method for culturing cells in accordance with claim 1, wherein the medium is essentially free of hypoxanthine and thymidine.

15. A method for culturing cells in accordance with claim 14, wherein the medium further comprises methotrexate.

16. A method for culturing CHO cells which comprises culturing and growing Chinese hamster ovary cells in the absence of serum in a medium comprising an osmolality regulator to maintain the osmolality of the medium within the range of about 200–350 mOsm, a buffer to maintain the pH of the medium within the range of about 6.5 to 7.5, about 1000–10,000 mg of a monosaccharide, about 400–600 mg of L-glutamine, about 10–200 mg of at least one amino acid selected from the group consisting of L-alanine, L-arginine, L-asparagine, L-aspartic acid, L-cystine, L-glutamic acid, glycine, L-histidine, L-isoleucine, L-leucine, L-lysine, L-methionine, L-phenylalanine, L-proline, L-serine, L-threonine, L-tryptophan, L-tyrosine and L-valine, about 0.25–5 mg of an inorganic or recombinant iron source, about 5 µg–5 mg of a recombinant or synthetic insulin and sufficient water to provide one liter of medium.

17. A method for culturing CHO cells which comprises culturing and growing Chinese hamster ovary cells in the absence of serum in a medium comprising a base medium containing the amino acids, non-ferrous metal ions, vitamins and cofactors essentially as set forth in Table 1, an osmolality regulator selected from NaCl, KCl, and $KNO_3$ in an amount sufficient to maintain the osmolality of the medium within the range of about 200–350 mOsm, at least one buffer selected from $CaCl_2.2H_2O$, $MgSO_4.7H_2O$, $NaH_2PO_4.2H_2O$, sodium pyruvate, N-[2-hydroxyethyl]piperazine-N'-[2-ethanesulphonic acid] (HEPES) and 3-[N-morpholino]-propanesulfonic acid (MOPS) in an amount sufficient to maintain the medium within the pH range of about 6.5–7.5, about 1000–10,000 mg of mannose, fructose, glucose or maltose, about 5 ml of 200 mM L-glutamine, about 50 mg each of L-proline, L-threonine, L-methionine, L-cysteine and L-tyrosine, about 20–50 mg of L-ascorbic acid, about 0.01–0.5 mg each of Vitamin B6 and Vitamin B12, about 0.25 –5 mg of a ferric or ferrous salt, about 1 mg of zinc sulfate, about 2.5 µg of copper sulfate, about 10,000–100,000 IU of at least one antibiotic selected from the group consisting of polymyxin, neomycin, penicillin and streptomycin, about 3 µl of ethanolamine, about 0.01–1.0 mg of putrescine, about 5 µg–5 mg of recombinant insulin and sufficient water to comprise one liter of medium; wherein each component of said medium is obtained from a source other than directly from an animal source.

18. A method in accordance with claim 1, wherein each component of the medium is selected from an inorganic, synthetic, recombinant, plant or bacterial source.

* * * * *